(12) United States Patent
Dodge et al.

(10) Patent No.: US 7,574,261 B2
(45) Date of Patent: *Aug. 11, 2009

(54) ELECTRICAL CURRENT INDUCED INHIBITION OF BONE GROWTH

(75) Inventors: George R. Dodge, Philadelphia, PA (US); J. Richard Bowen, Wilmington, DE (US)

(73) Assignee: Nemours Biomedical Research, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/439,141

(22) Filed: May 24, 2006

(65) Prior Publication Data

US 2006/0212088 A1 Sep. 21, 2006

Related U.S. Application Data

(63) Continuation of application No. 10/716,862, filed on Nov. 20, 2003, now Pat. No. 7,206,638.

(60) Provisional application No. 60/427,565, filed on Nov. 20, 2002.

(51) Int. Cl.
*A61N 1/32* (2006.01)
(52) U.S. Cl. .......................................... 607/43; 607/51
(58) Field of Classification Search .............. 604/21; 607/43, 50–52, 1–3, 59–76; 128/898
See application file for complete search history.

(56) References Cited

U.S. PATENT DOCUMENTS

| 3,842,841 | A | * | 10/1974 | Brighton et al. | 607/52 |
|---|---|---|---|---|---|
| 4,333,469 | A | * | 6/1982 | Jeffcoat et al. | 607/5 |
| 4,461,300 | A | * | 7/1984 | Christensen | 607/50 |
| 4,467,809 | A | * | 8/1984 | Brighton | 607/51 |
| 4,506,673 | A | * | 3/1985 | Bonnell | 607/50 |
| 4,683,896 | A | * | 8/1987 | Herbst et al. | 607/116 |
| 5,056,518 | A | * | 10/1991 | Pethica et al. | 607/2 |
| 5,458,558 | A | | 10/1995 | Liboff et al. | |
| 6,120,502 | A | | 9/2000 | Michelson | |
| 6,605,089 | B1 | | 8/2003 | Michelson | |
| 6,704,605 | B2 | | 3/2004 | Soltis et al. | |
| 6,966,911 | B2 | * | 11/2005 | Groiso | 606/75 |
| 7,206,638 | B2 | * | 4/2007 | Dodge et al. | 607/43 |

OTHER PUBLICATIONS

Minkin et al., "The effect of direct current on bone." Clin Orthop Relat Res. Mar.-Apr. 1968;57:303-9.*
Friedenberg et al., "The effect of direct current on bone." Surg Gynecol Obstet. Jul. 1968;127(1):97-102.*

* cited by examiner

*Primary Examiner*—Kennedy J Schaetzle
*Assistant Examiner*—Jessica Reidel
(74) *Attorney, Agent, or Firm*—Townsend and Townsend and Crew LLP

(57) ABSTRACT

A method and device the may be employed for inhibiting bone growth, including inducing epiphysiodesis or hemiepiphysiodesis, by applying electrical current to a desired region. The device includes a power source and one or a series of electrodes for applying a current sufficient to reduce or stop the growth of a bone to selected regions of the bone. The method and device may be used to correct growth discrepancies in extremities such as the arms or legs, as well as correct the curvature of the spine in scoliosis patients.

18 Claims, 9 Drawing Sheets

Week 1

Week 3

Week 6

Week 6 (Erect A/P)

Normal rabbit spine

Erect A/P  A/P

Histologic analysis for evidence of growth inhibition after 2 weeks of current

Histological analysis

Reduced volume of whole growth plate in high current group (50 µA)

ELECTRICAL CURRENT INDUCED INHIBITION OF BONE GROWTH

This application is a continuation of U.S. application Ser. No. 10/716,862 filed on Nov. 20, 2003 now U.S. Pat. No. 7,206,638 which is based on and claims priority to U.S. Provisional Patent Application No. 60/427,565, filed Nov. 20, 2002, herein incorporated by reference in its entirety.

BACKGROUND OF THE INVENTION

Many children have abnormalities in bone growth that lead to a variety of conditions such as scoliosis or disproportional long bone growth, such as in the legs or arms. For children suffering from scoliosis, if the curvature of the spine is severe enough, the child will require surgery to correct the curvature of the spine. The surgery typically involves the fusion of one or more vertebrae of the spine together to correct the curvature. Spinal surgery is complicated, high risk, costly, and requires a long period of convalescence.

Correcting disproportionate bone growth in an extremity is typically accomplished by performing an epiphysiodesis, which disrupts or destroys a selected growth plate for the purpose of delaying the longitudinal growth of the involved extremity. For example, a child may have a leg length discrepancy of 1 inch, which may be treated by performing an epiphysiodesis of a selected growth plate of the longer leg at a selected age. The epiphysiodesis of the selected growth plate inhibits residual longitudinal growth of the longer leg, and, as the child continues to grow, the continued growth of the shorter leg decreases the discrepancy. Timing of the current techniques is important since typically this ablation is permanent and its performance must be closely linked with the natural termination of growth.

One procedure for perforating an epiphysiodesis is the Phemister technique. This technique involves making two to three inch incisions placed medially and laterally on the extremity in the area of the growth plate. The growth plate is surgically explored and destroyed at its peripheral margins. More commonly used is a percutaneous method of epiphysiodesis that was developed at the A.I. duPont Hospital for Children. The percutaneous method involves malting a 5 mm incision directly over the growth plate through which a curette is introduced into the physis and is ablated. With these procedures, the patient needs postoperative protection by casting and restriction of activities for three to four months. These techniques are typically permanent and require careful timing with the natural growth of the child. If the procedure is too early, it will result in the creation of a length discrepancy for over growth of the untreated bone.

There is a need for alternative procedures for correcting abnormal bone growth in an individual and in particular, an alternative method for correcting the curvature of the spine in individuals suffering from scoliosis.

SUMMARY OF THE INVENTION

The invention is directed to electrical current induced inhibition of bone growth. The invention is directed to a device and method for reducing or arresting the growth of a bone that is an alternative to the above-described procedures.

Accordingly, the invention includes a device for reducing the growth of a bone where the device may include a power source for generating a current, where the current is effective to reduce the growth of a bone, and where at least one electrode is in electrical communication with the power source. The electrode is adapted to apply the current to a predetermined location of the bone. The device may include a controller in electrical communication with the power source and the electrode where the controller distributes a predetermined current to the electrode. The controller may be programmable and regulate the amount of the current applied to each of the at least one electrode, and the frequency and duration the current is applied to each of the electrodes.

The invention may also include a method for reducing the growth of a bone, comprising applying bone growth reducing electrical current m at least a portion of the growth plate of a bone, where the current is effective m reduce the growth of the bone in the applied region. The method may include positioning at least one electrode in or near the growth plate of the bone, where the bone growth reducing electrical current is applied to the growth plate through the electrodes. The method may also include providing a power source and controller in electrical communication with the electrodes, where the power source generates the bone growth reducing current and the controller regulates the amount of the current applied to each of the electrodes. The method may further include monitoring the change in growth of the bone. Still further the method may include determining an amount of correction for the bone, and removing the electrodes from the growth plate of the bone when the amount of correction has been achieved.

The invention may also include a method for correcting the curvature of the spine, comprising the steps of positioning at least one electrode at a portion of a vertebrae near the outside curve of the spine and applying a bone growth reducing current to the portion of the vertebrae, where the current is effective to reduce the growth of the vertebrae at the outside of the curve without reducing growth of the vertebrae near the inside of the curve. The method may include determining the amount of correction for the curvature of the spine, monitoring the change in curvature of the spine, and removing the at least one electrodes from the vertebrae when the amount of correction for the curvature of the spine has been achieved. Further, the method may include providing a power source and controller in electrical communication with the at least two electrodes, where the power source generates the bone growth reducing current and the controller regulates the amount of the current applied to each of the at least one electrode. Still further, the method may include providing at least one second electrode on a portion of the vertebrae along the inside of the curve of the spine, and applying a bone growth stimulating current to the at least one electrode.

DETAILED DESCRIPTION OF EMBODIMENTS OF THE INVENTION

The invention is directed to a method and device for using electrical current to reduce or stop the growth of selected regions of an actively growing bone. When a bone is actively growing, growth of the bone occurs at the end of the bone at the growth plate, also sometimes referred to as the physis. Stopping the growth of the bone across the entire growth plate is generally referred to as epiphysiodesis. Stopping the growth of a portion of the bone is generally referred to as hemiepiphysiodesis. The method and device of the invention may be used to induce hemiepiphysiodesis at selected regions of an actively growing bone or to induce epiphysiodesis across the entire bone. The growth inhibition can be complete, permanent or temporary and when temporary the inhibition can be reversed and the bone permitted to grow unabated.

The present invention involves the application of an electrical current to reduce or arrest bone growth. As will be discussed in more detail below, current may be used to reduce or arrest bone growth in the region of the bone where the current was applied. The level or amount of current may vary depending on such factors as the type of bone, the size and shape of the area of the bone to be treated, and the desired amount of reduction in bone growth. For many situations, 50 micro amps (μA) is effective to arrest the growth of at least a portion of the bone.

As discussed above, presently available procedures typically result in permanent ablation of the growth plate. The invention may reduce or arrest bone growth in a temporary or permanent manner by the use of electrical current. The current can be delivered to the affected a tea and effect or inhibit bone growth with the potential of being reversible such that when the degree of correction is achieved, the electrical current can be removed or terminated and the bone can potentially continue to grow.

Figure 1A:
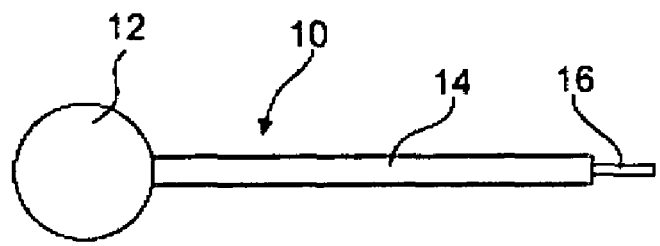
FIG. 1a is a diagram of a device in accordance with an embodiment of the invention.

With reference now to FIG. 1a, there is shown a device for arresting the growth of a bone, the device generally designated by the reference numeral 10. The device includes a power source 12 for generating a current. The power source 12 may be a battery, replaceable or rechargeable, set or controllable including remotely and prior to placement or implantation. The power source 12 may also be a plug-in type connection. The power source 12 should to be able to generate a current effective to reduce or meet bone growth for the selected application. In some embodiments, the device 10 may include one or more power sources 12 as necessary to apply the desired current for a particular application.

Emanating from the power source is at least one lead 14. The lead 14 is in electrical communication with the power source 12 and delivers current from the power source to at least one electrode 16.

Figure 1B:
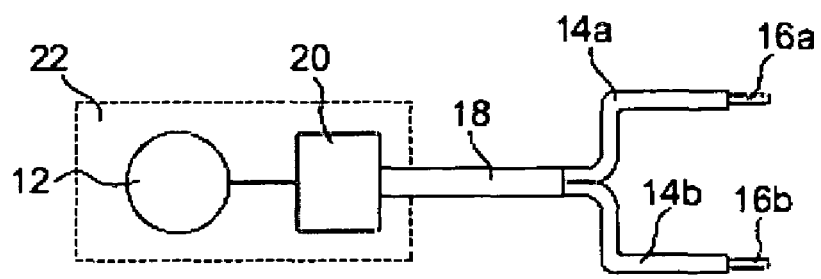
FIG. 1b is a diagram of a device in accordance with another embodiment of the invention.

The present invention may also include a device that has more than one lead and electrode. FIG. 1b illustrates an embodiment of the invention that has more than one lead 14 and more than one electrode 16. The power source 12 is similar to that described above and the particular options above are relevant here. The power source 12 provides the current for each electrode 16. The particular configuration of the leads 14 may be variable as long as the configuration allows for appropriate current to be delivered to each electrode 16 from the power source 12. By way of non-limiting examples, as shown in FIG. 1b, the leads 14 may be gathered as part of a single line 18 between the power source 12 and electrodes 16. Alternatively, there may be a single line emanating from the power source and dividing into one or more leads. As discussed above, the leads 14 must be capable of transferring current from the power source to the electrode 16. According to an embodiment of the invention, the lead 14 may be an electrically conductive wire covered by an insulating sheath. The lead and sheath may be constructed of a material suitable for use and implantation in humans and other living beings.

Figure 1C:
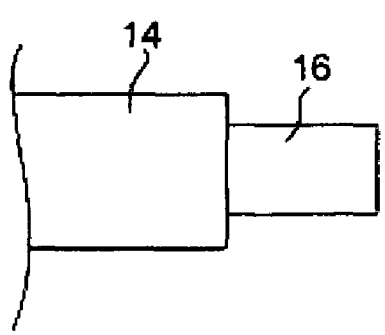
FIG. 1c is a diagram of an electrode in accordance with an embodiment of the invention.
Figure 1D:
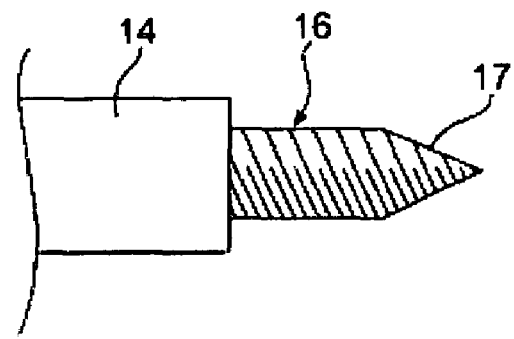
FIG. 1d is a diagram of an electrode in accordance with another embodiment of the invention.

The lead 14 transfers electrical current to the electrode 16. The electrode 16 transfers or delivers the current to the selected region of the bone. With reference now to FIGS. 1c and 1d, a variety of configurations of the electrode 16 may be utilized. The electrode 16 may be an exposed end of the lead 14 as shown in FIG. 1c. Alternatively, the electrode 16 may be an electrically conductive end made from electrically conductive materials, such as electrically conductive wire, rods, and the like. In other embodiments, the electrode 16 may be configured with a threaded end 17. The threaded end may be electrically conductive and may be part of the electrode 16 for applying current to the bone. As will be discussed below, the threaded end 17 may be used in securing the electrode in a position within the bone. In certain embodiments, the electrode 16 is preferably long enough to be in contact with or inserted into the growth plate of the bone to be treated.

The device 10 is designed to deliver sufficient current to reduce or arrest the growth of a bone. The combination of the power source 12, the one or mom leads 14, and the electrodes 16 provides a current to the selected region of the bone sufficient to reduce or arrest the growth of the selected region of the bone. The amount of current required will vary depending on such factors as the type of bone, the size of the growth plate, and the individual. The current must be higher than that required to stimulate the growth of the bone. According to an embodiment of the invention, a current of at least 50 μA will reduce the growth of at least a portion of a bone.

With reference to FIG. 1b, a current controller 20 may be used to control the current applied to each electrode 16. The controller 20 may deliver the same current to each electrode 16a and 16b or vary the current delivered to each electrode using two separate leads 14a and 14b tethered together as illustrated in FIG. 16. The controller 20 may also operate to control the amount of time the current is applied at each electrode 16. For example, the controller may be programmed to apply 35 μA to certain electrode 16a for 3 seconds at 5 second intervals and 50 μA to other electrode 16 for 5 seconds at 2 second intervals. The controller 20 may be programmed externally or by radio frequency communication from a computer. Further, some embodiments of the device 10 may include one or more controllers 20. The controller 20 and power source 12 may be part of the same unit 22 from which one or more leads 14 emanate.

Figure 2A:
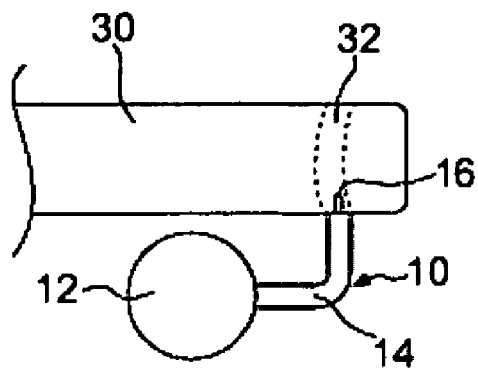
FIG. 2a is a diagram of a device in accordance with an embodiment of the invention with the electrode positioned in a bone.

With reference now to FIG. 2a, there is shown an embodiment of the device 10 having a power source 12, a single lead 14, and electrode 16. The electrode 16 should be in electrical contact with the region of the bone to be treated. In FIG. 2a, the electrode 16 has been positioned in the growth plate 32 of the bone 30 to be treated. In small areas with relatively small bones, one electrode 16 positioned near the growth plate may be sufficient.

Figure 2B:
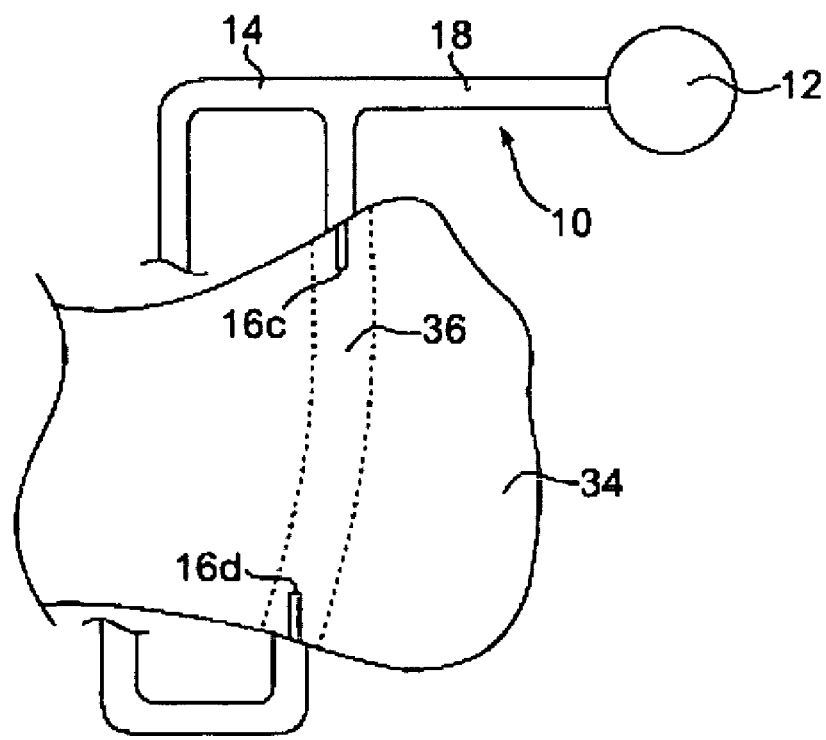
FIG. 2b is a diagram of the yet another device in accordance with an embodiment of the invention with more than one electrode positioned in a bone.

Turning now to FIG. 2b, there is shown a device 10 having a power source 12 and two leads 14 and two electrodes 16c and 16d. The electrodes 16c and 16d are positioned in the bone 34, near the growth plate 36 such that electrical current is applied across the entire growth plate 36. Depending on the size of the bone and growth plate, more than two electrodes may be utilized to inhibit the growth of the bone.

The electrodes may be located such that the current from the electrodes affects the growth plate to inhibit growth of the bone either permanently or temporarily. This location may be next to the growth plate, in close proximity to the growth plate, or directly in the growth plate to inhibit growth of the bone. The electrodes 16 may be inserted percutaneously or through other surgical procedures.

The power source 12 and the controller 20 may be implanted within the patient or may be kept external. Keeping the power source 12 and controller 20 external allows for easy replacement of the power source and reprogramming of the controller. If the power source 12 and controller 20 are implanted in the patient, the controller may be preprogrammed prior to implantation. Further, the controller 20 may be programmable by wireless or other suitable communication from an external source, e.g., a computer.

The invention maybe implanted in a patient by general surgical methods. The electrodes may be implanted in the patient percutaneously. Typically, a small hole is prepared in the bone for the electrode to be inserted. The hole is small enough such that the electrode may be secured in the hole by pressure fit between the electrode and the walls of the hole in the bone. Alternatively, the electrode may be secured in place using a biological adhesive or fibrin adhesive. As discussed above, if the electrodes have threaded ends, the electrodes may be secured in the holes by rotating the electrodes in the hole such that the threads of the electrode catch on the inside walls of the hole. The battery and optional controller may be implanted subcutaneously or left externally, each with appropriate grounding.

A method for inhibiting the growth of a bone includes placing one or more electrodes 16 within or in close proximity to the growth plate of the bone in which growth is to be reduced or arrested. A current is applied to the growth plate through the implanted electrodes. The current should be high enough to inhibit, reduce, or stop bone growth of the treated bone. If the current is not high enough or the electrode is not positioned to apply current across the entire growth plate, growth of the bone will be reduced in the region where the current is applied, but the remainder of the bone will continue to grow resulting in uneven growth across the region of the bone. This may be desirable in the case of effecting disproportional growth such as that resulting in curves in bone, such as in the vertebral bodies of the spine. In other conditions and more typically, in limb length discrepancies, growth arrest or inhibition is required across the bone and balanced inhibition of growth across the bone is necessary.

Depending on the size of the bone or growth plate, one or more electrodes 16 may be used to ensure current across the desired region to inhibit growth of the bone. The invention may be used with virtually any bone or bone containing extremity that is growing in an individual including, but not limited to, ribs, the jaw, bones of the arm, bones of the leg, bones of the foot, bones of the hand, and vertebrae in the spine. The current may be applied continuously or intermittently for a period of time until the desired growth stoppage has been achieved. This can be assessed by non-invasive imaging techniques including, but not limited to, X-ray imaging, magnetic resonance imaging (MRI), and computed tomography (CT) scans. For example, in an application to treat uneven growth for extremities such as the arms or legs, the electrodes are implanted in the longer extremity. The electrodes are positioned such that current is applied across the entire growth plate. Current effective to inhibit bone growth is applied across the growth plate. The amount of time the current is applied may vary widely depending on such factors as the size of the patient and the difference in length of the extremities. Once the treatment has been concluded, the electrodes 16 and the device 10 are removed from the patient Portions such as the electrodes could be left inside without detriment to the patient, as is much orthopedic hardware.

The invention includes a device and method for correcting the curvature of a spine. The method involves reducing the growth of a portion of one or more vertebrae located in the curving region of the spine. Specifically, the portion of the vertebrae located near the outside of the curving region is targeted for reducing or arresting growth of that portion of the vertebrae. The portion of the vertebrae on the inside of the curve is thus allowed to grow. As the portion of the vertebrae on the inside of the curving region of the spine grows, while the portion of the vertebrae on the outside of the curving region slows or stops, the curvature of the spine is reduced.

Figure 3:
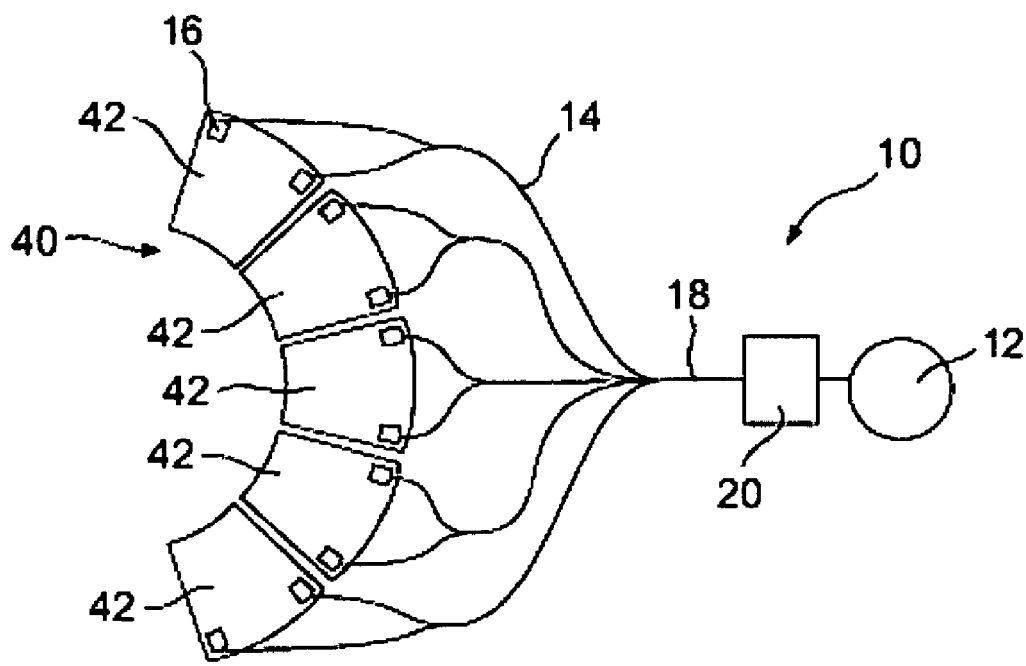
FIG. 3 is a diagram of a device in accordance with another embodiment of the invention configured for correcting the curvature of the spine.

With reference now to FIG. 3, there is shown the device 10 discussed above configured for treating the curvature of the spine 40. In FIG. 3, the device 10 includes ten leads 14 and ten electrodes 16. The number of leads and electrodes can be varied and is not particularly limited. The electrodes 16 are located at one or more vertebrae 42 in the curving region of the spine 40. The electrodes 16 are positioned near the outside of the curve of the spine. Preferably, the electrodes 16 are positioned starting at the vertebrae at the center or apex of the curve and are placed on adjacent vertebrae extending in both directions from the earner or apex of the curve. The electrodes 16 are positioned such that the growth of the portion of the vertebrae 42 near the outside of the curve is slowed or arrested, without stopping the growth of the same vertebrae on the inside of the curve. Preferably, a small hole is made in the vertebrae 42 for receiving the electrodes 16. The electrodes 16 can remain permanently in place without complication much like the rods and implants in conventional surgical approaches, or the electrodes can be removed once the desired correction is achieved. The procedure requires operative placement of the electrodes from the multiple leads as required to each involved growth plate by thoracoscopy, thoracotomy, laparotomy, laparoscopy, or by radiographic or CT image guidance.

Current generated from the power source 12 is applied to the vertebrae in the selected region. The current should be high enough to stop or reduce growth in the selected region without stopping growth across the entire vertebrae. The current applied to each electrode 16 may vary. For example, the electrode at the apex of the curve may receive more current for longer durations than the electrodes on adjacent vertebrae. The vertebrae on each side of the apex may require less correction and may receive less current or less treatment time to achieve a corrective result. The controller 20 may be programmed to contain algorithms for applying the desired amount of current and the duration of the current to each electrode 16 for each vertebrae and may require one or more power supplies, i.e., batteries. The control of the power can be programmed in the controller 20 or be set to be remote controlled according to the outcome monitored by radiographs and MRI.

Figure 4:
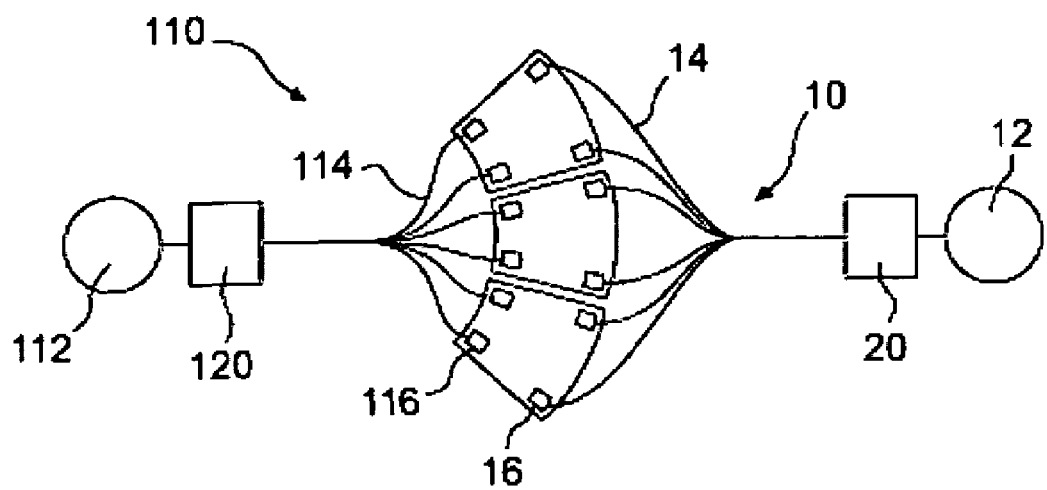
FIG. 4 is a diagram of a device in accordance with yet another embodiment of the invention for correcting the curvature of the spine.

In another embodiment, a set of electrodes for stimulating the growth of the vertebrae may be located on the inside of the curvature of the spine as shown in FIG. 4. FIG. 4 shows the installation of a separate device 110 containing a power source 112 and controller 120 connected to one or more leads 114 and electrodes 116. In this embodiment, the electrodes 116 are located at the vertebrae near the inside region of the curve. The electrodes apply a low current to stimulate growth of the vertebrae in this region. The current may be under 20 µA and may range from 10 µA to 20 µA. The electrodes 16 may be controlled by a separate power source 112 and controller 120 or may alternatively be controlled by a single device using controller 20 and power source 12.

The device 10 and 110 maybe implemented by one of several procedures depending on where the electrodes are to be placed. The procedure requires operative placement of the electrodes from the multiple leads as required to each involved growth plate by thoracoscopy, thoracotomy, laparotomy, laparoscopy, or by radiographic or CT image guidance. For treating curvature of the spine, the leads 14, the power supply 12, and the controller 20 may optionally be contained in a chest tube or drainage tube. Alternatively, the power supply 12 and controller 20 maybe located outside the patient for easy access as discussed above.

Certain aspects of the invention will be further described in the following non-limiting examples.

EXAMPLE 1

Spinal Curvature

Figure 5:
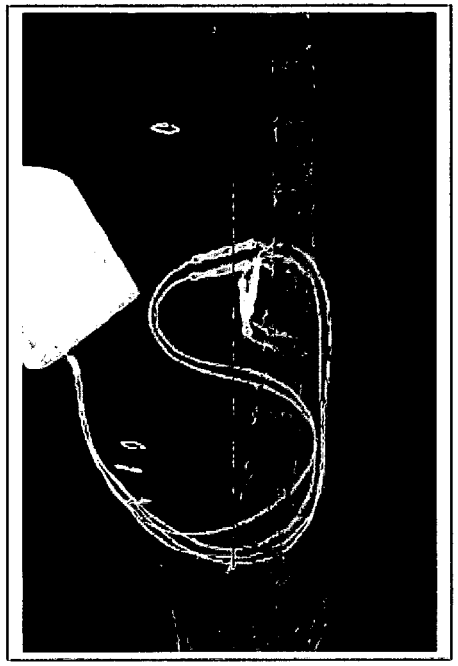
FIG. 5 is a series of spinal x-rays taken over a six week period according to an embodiment of the invention.
Figure 5:
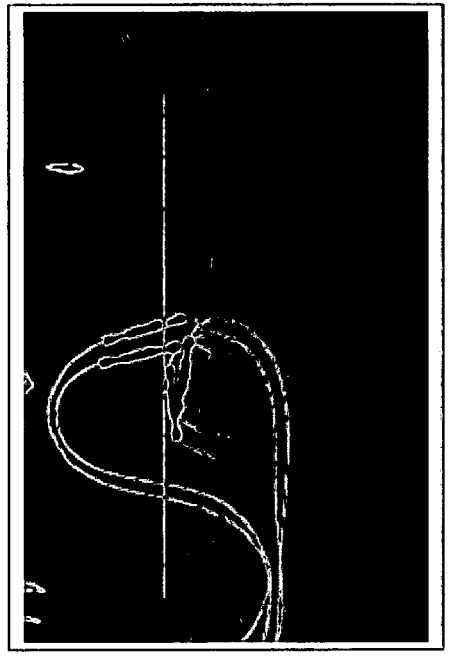
Figure 5:
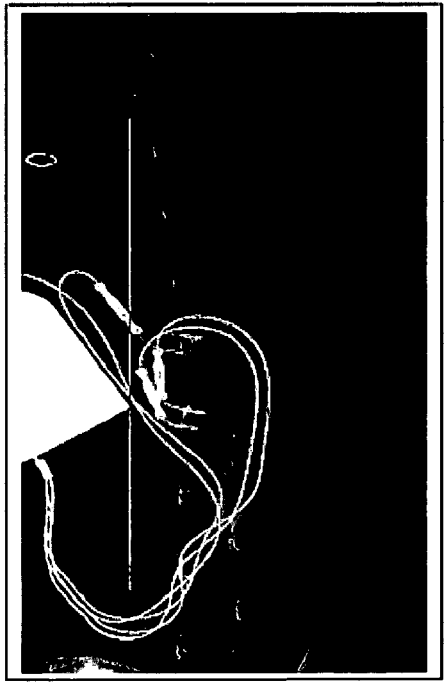
Figure 6:
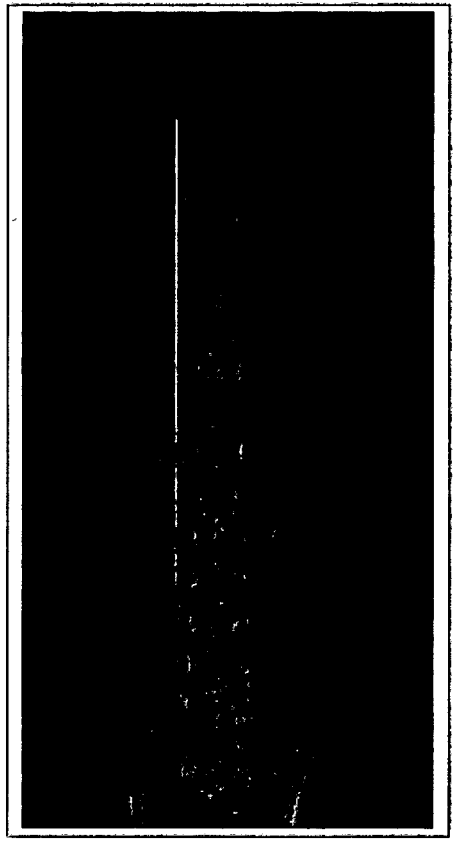
FIG. 6 shows two spinal x-rays from a control group according to an embodiment of the invention.
Figure 6:
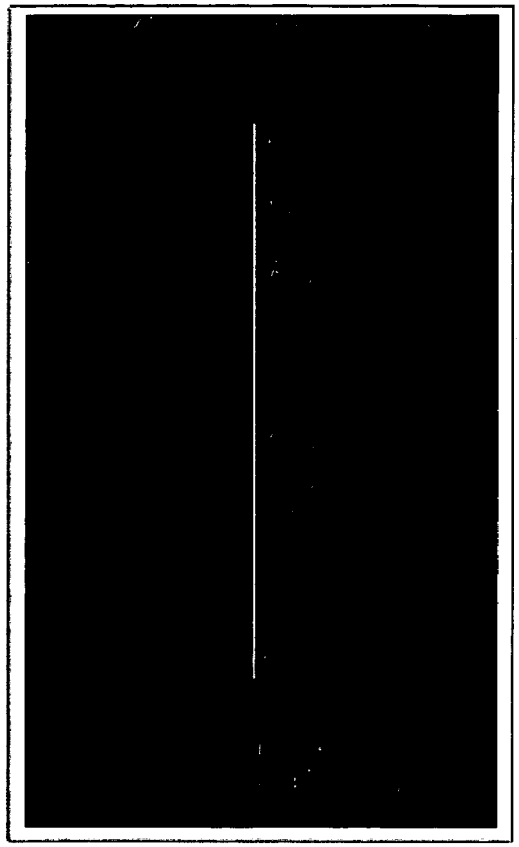

According to an embodiment of the invention, performing a hemiepiphysiodesis in the spine may correct or lessen scoliosis or curves of the spine. If a curve can be created in the spine using current applied to the growth plate in the lateral or left aspect of multiple vertebral bodies, then the electrical current could be applied m the apex of an existing curve and correct the curve or permit bone growth in the opposite direction. FIGS. 5 and 6 illustrate the result of an experiment using an Institutional Animal Use and Care Committee-approved protocol with an immature rabbit. The growth of the spine was tested to determine if it could be altered in a unilateral manner by placing electrodes unilaterally in the region of four epiphyseal plates of three vertebral bodies. FIG. 5 illustrates the progress of the spinal curve created over the 6 weeks studied. The evidence from the x-rays strongly suggests that the growth of the spine is being affected by the unilateral current. After the 50 µA in four vertebral growth plates for 6 weeks it is obvious that the spine is curving away from the side where the current is delivered. In the control group the spine remains straight during this time frame (FIG. 6). The x-rays were digitized and the height of the vertebral bodies was measured. The percent change in the size of the right to left vertebra was found in the normal untreated spine to be between 0.992%-1.015% while the vertebral size measured in the treated spine ranged from 2.5% to 9.5%.

EXAMPLE 2

Long Bone

According to an embodiment of the invention a fine-thread electrode was inserted into a left distal femur and a power source was implanted subcutaneously in three groups. The three groups of subjects comprised those receiving no current, those receiving a constant current of 10 µA (low-current, LC), and those receiving a constant current of 50 µA (high current, HC) and used modified Osteogen™ devices. At two weeks, the difference of femur lengths was measured with a digital caliper. Histologic changes were studied using hematoxylin-eosin and Safranin-O staining, including narrowing of the growth plate or its possible closure, bony bridges, and the cellular arrangement of various zones in the growth plate. The computerized histomorphometric analysis of the growth plate was performed and comparisons were made in three groups and both the femur receiving current ("operated") and the femur not receiving current ("non-operated") limbs.

Figure 7:
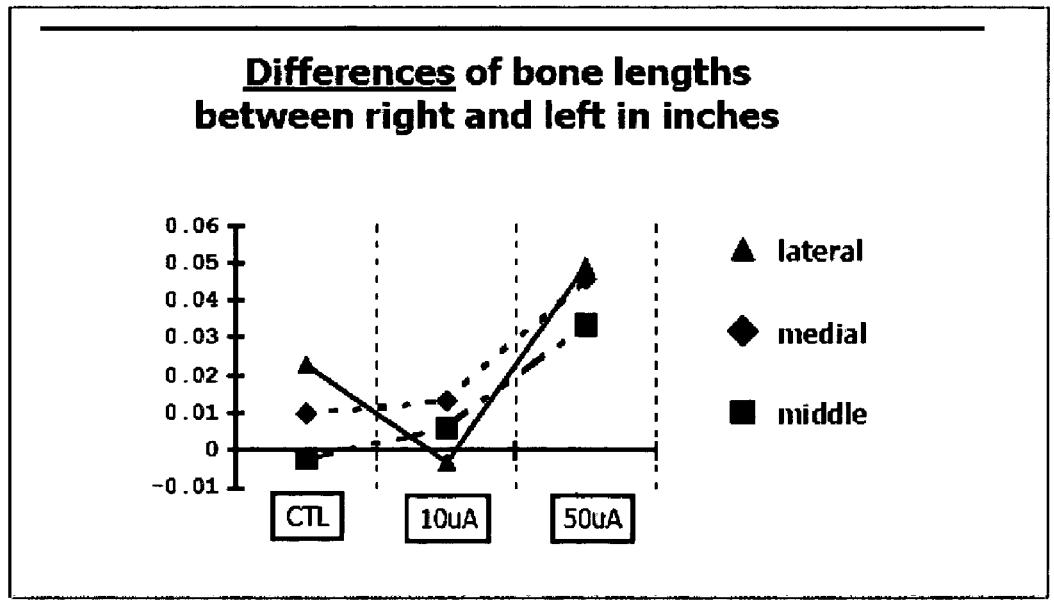
FIG. 7 is a graph illustrating differences in bone length according to an embodiment of the invention.
Figure 8:
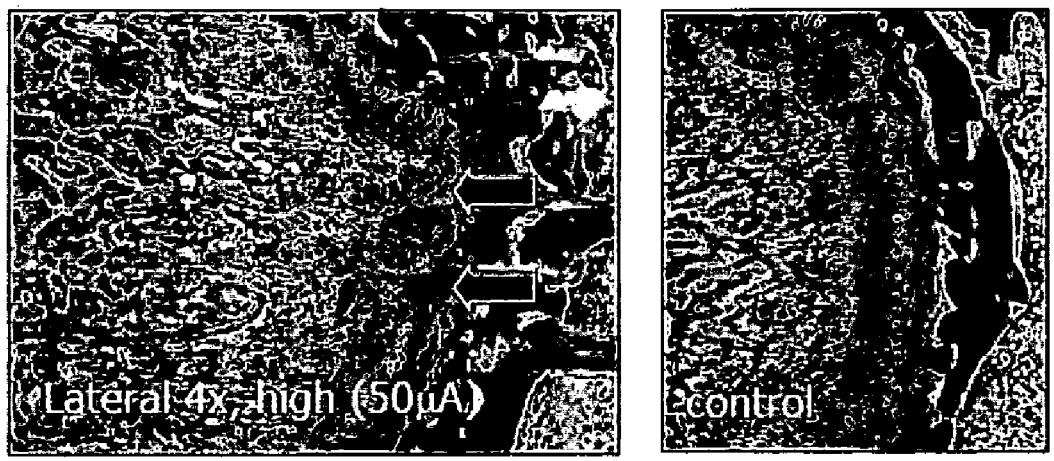
FIG. 8 illustrates a distorted structure of an epiphyseal plate and intermittent boney bridges indicating growth interruption and arrest according to an embodiment of the invention.
Figure 9:
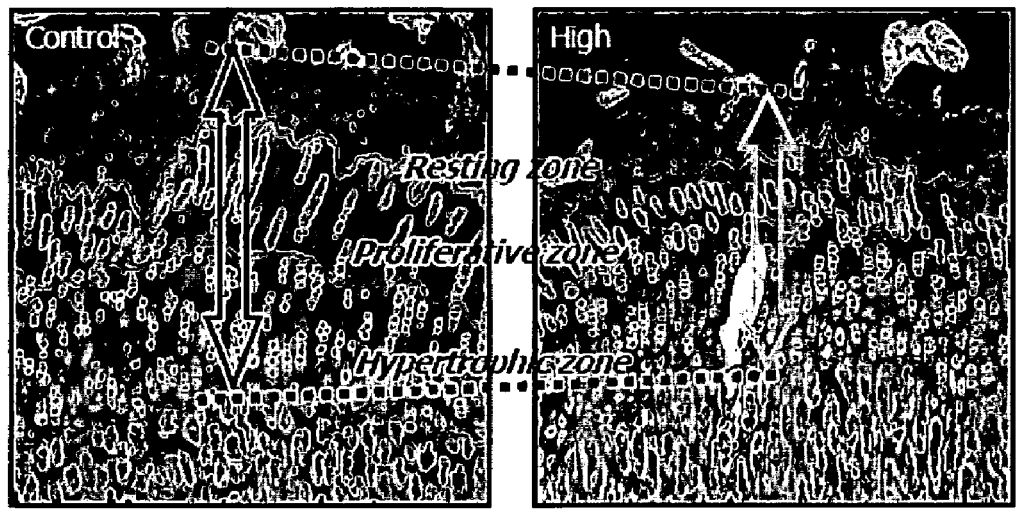
FIG. 9 illustrates the reduced volume of a whole growth plate according to an embodiment of the invention.

The difference in femur length was consistently larger in the HC group than those in other groups when comparing operated to control side. The growth of the operated limb in the HC group was inhibited by ~200% in comparison to control or LC groups as illustrated in the graph of FIG. 7. The most significant histologic finding was the appearance of putative bony bridges and some distorted internal structure of the growth plate in the HC group as illustrated in FIG. 8. The HC group also showed disorganized columnar arrangement and decreased lengths in the proliferative zones. Bony bridges or the same degree of disorganization could not be detected in the LC, or NC group. In the histomorphometric study, the volumes of whole growth plate, resting zone, and combined proliferative and hypertrophic zones in lateral or left (operated) side of the HC group were consistently smaller, by ~20% when compared to those of other groups as illustrated in FIG. 9.

The invention claimed is:

1. A device for reducing the growth of a bone, the device comprising:
    a power source for generating a current, wherein the current is effective to reduce the growth of a bone;
    at least one lead having a proximal end and a distal end wherein said lead extends from said power source at its proximal end to carry current from said power source; and
    at least one electrode having a proximal end and a distal end, said at least one electrode extending from the distal end of said lead from its proximal end, and wherein the distal end of said at least one electrode is free and is sized and configured to be implanted directly into a bone growth plate to apply the bone growth reducing current at least partially across an entire longitudinal dimension of the bone growth plate; wherein the longitudinal dimension of the bone growth plate extends along a direction perpendicular to a latitudinal or transverse direction of the bone growth plate extending from an epiphysis of the bone to a metaphysis of the bone.

2. The device of claim 1 wherein the at least one electrode comprises a plurality of electrodes in electrical communication with the power source.

3. The device of claim 1 wherein the at least one electrode comprises a threaded portion.

4. The device of claim 1 further comprising a controller in electrical communication with the power source and the at least one electrode, wherein the controller distributes a predetermined current to the at least one electrode.

5. The device of claim 4 wherein the controller regulates a frequency and duration of the current distributed to the at least one electrode.

6. The device of claim 4 wherein the controller regulates an amount of the current applied to each of the at least one electrode.

7. The device of claim 4 wherein the controller programmably regulates an amount of the current applied to each of the at least one electrode, and a current having a frequency and a duration is applied to each of the at least one electrode.

8. The device of claim 4 wherein the current is at least 50 µA.

9. The device of claim 1 comprising at least two electrodes and wherein the amount of current delivered to the at least two electrodes is different.

10. The device of claim 1 wherein the at least one lead comprises at least two leads.

11. The device of claim 1, wherein said at least one lead is split into at least two leads having at least two electrodes with one of said electrodes arranged at an end of each of said leads.

12. A device for reducing the growth of a bone, the device comprising:
  a power source for generating a current, wherein the current is effective to reduce the growth of a bone;
  at least two leads each having a proximal end and a distal end wherein each of said leads extends from said power source at its proximal end to carry current from said power source; and
  at least two electrodes each having a proximal end and a distal end, each of said electrode extending from the distal end of said lead from its proximal end, and wherein the distal ends are free and sized and configured to be implanted directly into longitudinally spaced sections of a bone growth plate to apply the bone growth reducing current across an entire longitudinal dimension of the bone growth plate; wherein the longitudinal dimension of the bone growth plate extends along a direction perpendicular to a latitudinal or transverse direction of the bone growth plate extending from an epiphysis of the bone to a metaphysis of the bone.

13. The device of claim 12 wherein at least one of the at least two electrodes comprise a threaded portion.

14. The device of claim 12 further comprising a controller in electrical communication with the power source and the at least two electrodes, wherein the controller distributes a predetermined current to the at least two electrodes.

15. The device of claim 14 wherein the controller regulates a frequency and duration of the current is distributed to the at least two electrodes.

16. The device of claim 14 wherein the controller programmably regulates an amount of the current applied to each of the at least two electrodes, and a current having a frequency and a duration is applied to each of the at least two electrodes.

17. The device of claim 12 wherein the current is at least 50 µA.

18. The device of claim 12, wherein said at least two leads are split into at least four leads having at least four electrodes with each one of said electrode at an end of each lead.

* * * * *